US00RE38299E

(19) United States
(12) Reissued Patent
Bolmsjö

(10) Patent Number: US RE38,299 E
(45) Date of Reissued Patent: Nov. 11, 2003

(54) APPARATUS FOR HEAT TREATMENT OF TISSUE

(75) Inventor: Magnus Bolmsjö, Lund (SE)

(73) Assignee: ProstaLund Operations AB, Lund (SE)

(21) Appl. No.: 09/945,574

(22) PCT Filed: May 17, 1996

(86) PCT No.: PCT/SE96/00649

§ 371 (c)(1),
(2), (4) Date: Nov. 14, 1997

(87) PCT Pub. No.: WO96/36288

PCT Pub. Date: Nov. 21, 1996

Related U.S. Patent Documents

Reissue of:
(64) Patent No.: 5,964,791
Issued: Oct. 12, 1999
Appl. No.: 08/952,260
Filed: Nov. 14, 1997

(30) Foreign Application Priority Data

May 18, 1995 (SE) ..... 9501875

(51) Int. Cl.[7] ..... A61F 2/00
(52) U.S. Cl. ..... 607/100; 607/102; 607/101; 606/49
(58) Field of Search ..... 607/100–102, 607/122; 606/5, 15, 41, 45, 49

(56) References Cited

U.S. PATENT DOCUMENTS

| | | | | |
|---|---|---|---|---|
| 3,977,408 A | | 8/1976 | MacKew | |
| 4,204,549 A | | 5/1980 | Paglione | |
| 4,311,154 A | | 1/1982 | Sterzer et al. | |
| 4,535,773 A | | 8/1985 | Yoon | |
| 4,676,258 A | | 6/1987 | Inokuchi et al. | |
| 5,222,953 A | | 6/1993 | Dowlatshahi | |
| 5,334,206 A | * | 8/1994 | Daikuzono | 606/7 |
| 5,366,490 A | | 11/1994 | Edwards et al. | |
| 5,421,819 A | | 6/1995 | Edwards et al. | |
| 5,464,445 A | * | 11/1995 | Rudie et al. | 607/101 |
| 5,500,012 A | * | 3/1996 | Brucker et al. | 607/122 |
| 5,623,940 A | | 4/1997 | Daikuzono | |
| 5,645,528 A | | 7/1997 | Thome | |
| 5,800,432 A | * | 9/1998 | Swanson | 606/49 |
| 6,016,452 A | | 1/2000 | Kasevich | |

FOREIGN PATENT DOCUMENTS

| | | |
|---|---|---|
| EP | 0370890 | 5/1990 |
| EP | 0462302 | 12/1991 |
| JP | 2121675 | 5/1990 |
| WO | WO9401177 | 1/1994 |

OTHER PUBLICATIONS

Jozef Mendecki, Ph.D., et al., *Microwave Applications for Localized Hyperthema Treatment of Cancer of the Prostate*, Technical Innovations and Notes, Nov. 1980, vol. 6, No. 11, pp. 1583 through 1588.

* cited by examiner

*Primary Examiner*—Roy D. Gibson
(74) *Attorney, Agent, or Firm*—John R. Ley

(57) ABSTRACT

A device for heat treatment of body tissue, including heating means (10) for local heating of the body tissue, and temperature sensing means (11) for sensing the tissue temperature, said heating means being enclosed in a catheter (12). A first temperature sensing means (11) is connected to a first carrier (13), which is made to be advanced through a first opening in catheter (12), and said first carrier (13) is equipped with a pointed tip for insertion into such body tissue that is to be heat-treated.

80 Claims, 3 Drawing Sheets

APPARATUS FOR HEAT TREATMENT OF TISSUE

Matter enclosed in heavy brackets [ ] appears in the original patent but forms no part of this reissue specification; matter printed in italics indicates the additions made by reissue.

TECHNICAL FIELD OF THE INVENTION

The invention concerns a device for heat treatment of body tissue in accordance with patent claim 1.

Certain conditions of illness with unnatural growth of body tissue are successfully managed by the use of heat treatment. The tissue is heated to such an extent that the tissue dies. Certain types of cancer and hyperplasia in the prostate gland are examples of such conditions of illness. During treatment certain parts of the tissue are to be treated whereas others must or should be protected.

STATE OF THE ART

Various devices may be used for the purpose of producing heat. Laser as well as microwave and RF antennas are commonly used. Because the volume of the tissue to be treated varies, as does the heat-absorption quality of both this first-mentioned tissue and adjacent tissue, which is not to be treated, it is appropriate that continuous control takes place during treatment.

It is commonplace that the means of heating comprises some kind of a temperature sensor, which is provided on the heat-producing element to sense the temperature of an adjacent tissue. A drawback of this design is that the temperature sensor lends information that is more pertinent to the temperature of the element than to that of the tissue.

An example of this type of heating device is shown and described in EP 0 370 890. The device comprises a microwave antenna enclosed in a catheter. The antenna is designed to emit electromagnetic energy to the tissue surrounding the antenna. The catheter is also equipped with cooling channels for cooling of the tissue closest to the catheter. There is provided a temperature transducer in the catheter to sense the temperature of the catheter. The temperature sensed therefore does not agree with that of the tissue to be treated.

Another example of this is to be found in U.S. Pat. No. 5,366,490. According to that patent specification, previously known heating devices present multiple drawbacks. The most critical of these drawbacks is that heating takes place in a diffusely defined area or volume. In particular systems comprising a microwave antenna in a catheter, it is specified, lead to great risks and worse treatment outcome because the area of treatment is not narrowly defined.

According to U.S. Pat. No. 5,366,490, it is therefore suggested that the means of treatment is provided in a needle which is advanceable so as to exit a catheter. The catheter and then the needle are controlled very accurately in place with the aid of an ultra sound device, which during the entire treatment continuously monitors the area of treatment. Control of the needle must be very precise since treatment efficiency is locally very high in the vicinity of the needle. The treatment is a surgical one. There are high demands on the person who carries out the treatment and on the surgical equipment required.

SUMMARY OF THE INVENTION

It is an objective of the present invention, when it comes to conventional types of heat treatment devices, to provide a device which eliminates the drawbacks of diffusely working heating means that are equipped with temperature sensors. The objective is achieved by the features indicated in claim 1. According to the present invention, registration of relevant temperature data from the body tissue is readily made possible. Treatment made possible through the device according to the invention may take place in an outpatient setting without the requirement of surgical staff and equipment or operation rooms.

DESCRIPTION OF THE INVENTION

Figure 1:
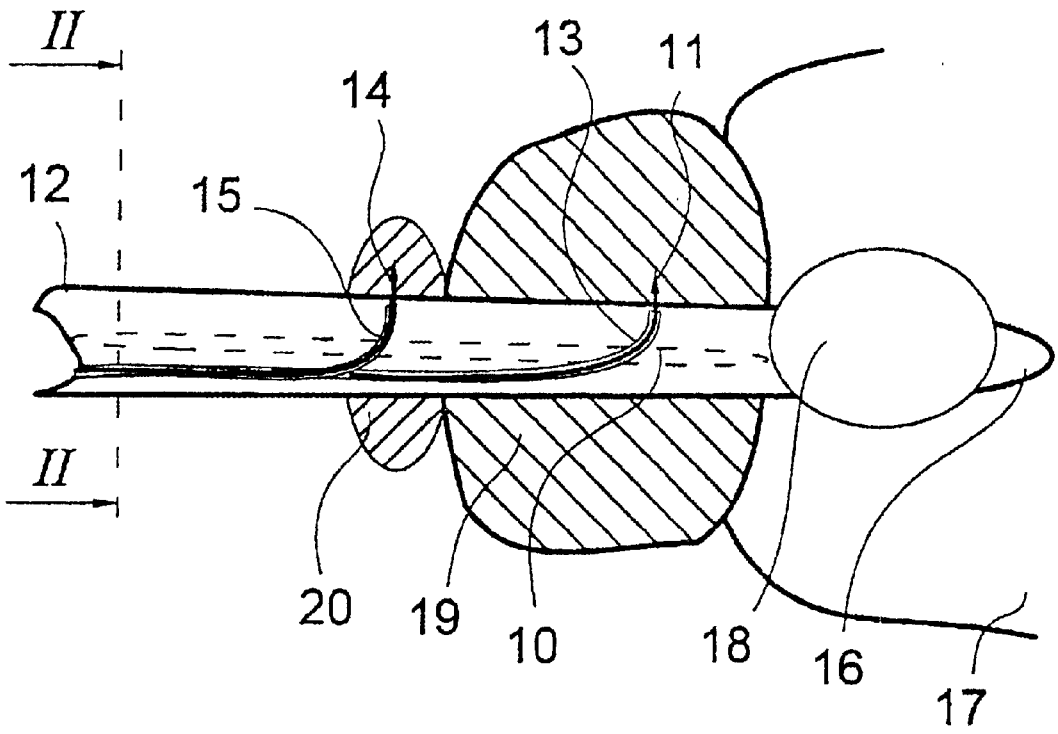
FIG. 1 is a side view partially in a cross-section of one embodiment of the device according to the invention.

In the embodiment schematically shown in FIG. 1, a catheter 12 has been inserted into the urethra in such a manner that a tip or apex 16 of catheter 12 has entered into the urine bladder 17. Prior to start of the treatment, a balloon 18 connected to catheter 12 is expanded inside the urine bladder. Unintentional extraction of the catheter 12 is thereby prevented. An external sphincter 20 schematically indicates such surrounding tissue which is not to undergo treatment.

Catheter 12 comprises means 10 for heating tissue in the prostate gland 19. In a preferred embodiment, the heating device 10 comprises an antenna for emission of electromagnetic energy. The antenna usually operates within the frequency range of 1 MHz–5000 MHz. In other embodiments, the heating device 10 comprises receptacles containing, a heated liquid. The heating may take place through circulation of the heated liquid through catheter 12, or through some form of a heating element in a direct connection to the receptacle. It is also possible to have the heating device 10 abut either directly to the tissue or indirectly via an intermediary device. The intermediary device may be so designed that it expands during heating, thus allowing for an improved abutment against the tissue, and improved heat transmission as well.

In yet other embodiments, the heating device 10 may comprise one or several smaller radio frequency electrodes provided externally on the catheter. A larger electrode interacts with the catheter electrode in such a way that it is heated by the transmitted radio energy.

An active portion of the heating device 10 is located in the prostate gland 19. Supply of the energy, which is to be emitted to the tissue, preferably occurs in channels in catheter 12. Below, these will be described in more detail with reference to FIG. 2.

In the course of an ongoing treatment the tissue is heated. Heating should occur within certain temperature intervals for the sake of optimal treatment results. If the temperature is too elevated, unnecessary severe damage is inflicted on the tissue. If the temperature is too low, on the other hand, the desired treatment result is not achieved. In order to be directly able to register temperature increase in the tissue to be treated a first temperature sensing means 11 is connected to a first carrier 13. Carrier 13 is run through a channel in catheter 12 and is provided so as to be advanced through an opening in catheter 12. Preferably, there is provided a guide for carrier 13 in the opening of the catheter, so as to guide carrier 13 out and into the tissue at a desired angle relative to catheter 12. Carrier 13 may also run in a tubing in the catheter. The guide includes a sloping or inclined portion, against which the carrier 13 can be brought and, thus, be angled out and, upon further advancement, moved away from the catheter. The carrier 13 is constructed of a relatively stiff material, thus facilitating penetration and insertion into the tissue.

Either carrier 13 or temperature sensing means 11 is equipped with a tip, which allows for a more simplified insertion into the tissue. Temperature sensing means 11 may be either conventionally designed as a resistive transducer or a semi-conductor. The cable drawing required for such transducers is preferably carried out through catheter 12. If an optical type of transducer is used, a fiber optic conductor is provided through catheter 12.

Advancement of the temperature sensing means 11 or its carrier 13 out of catheter 12 is controlled by control means from the exterior of the catheter outside of the body. This should preferably occur in a well defined way so that insertion into the tissue is implemented down to the desired depth. In a simple design, carrier 13 is made as a stiff tube ending in a tip and is provided to extend through a channel in catheter 12. Temperature sensing means 11 is provided at one end of carrier 13. At the other end, carrier 13 is equipped with a handle. The channel and carrier 13, which is contained in the channel, are given such dimensions and such a bending resistance that the degree of advancement becomes well defined in relation to the longitudinal advancement of the carrier. The advancement by maneuvering of the handle and carrier is limited by a stop or some arresting means so as to avoid the risk of the temperature sensing means 11 passing beyond the desired area of temperature sensing.

By continuously sensing of the temperature in the tissue being treated, it is possible to accurately control supplied power and the end result. Thus, the risk of undesired damage to the tissue is significantly diminished.

In order to further lessen the risk of damage, and more specifically in such surrounding tissue which shall not be reached through treatment, a second temperature sensing means 14 is connected to a second carrier 15. This second carrier 15 is designed to be advanced through and out of catheter 12 at a certain distance from the first carrier 13 in the longitudinal direction of the catheter 12. The distance is determined by the size of the treatment area and is ample enough to allow temperature sensing means 14, in its forwardly advanced state, to penetrate into such a tissue which should not be damaged during treatment. In the shown embodiment the second temperature sensing means 14 measures the temperature in the sphincter 20.

Figure 2:
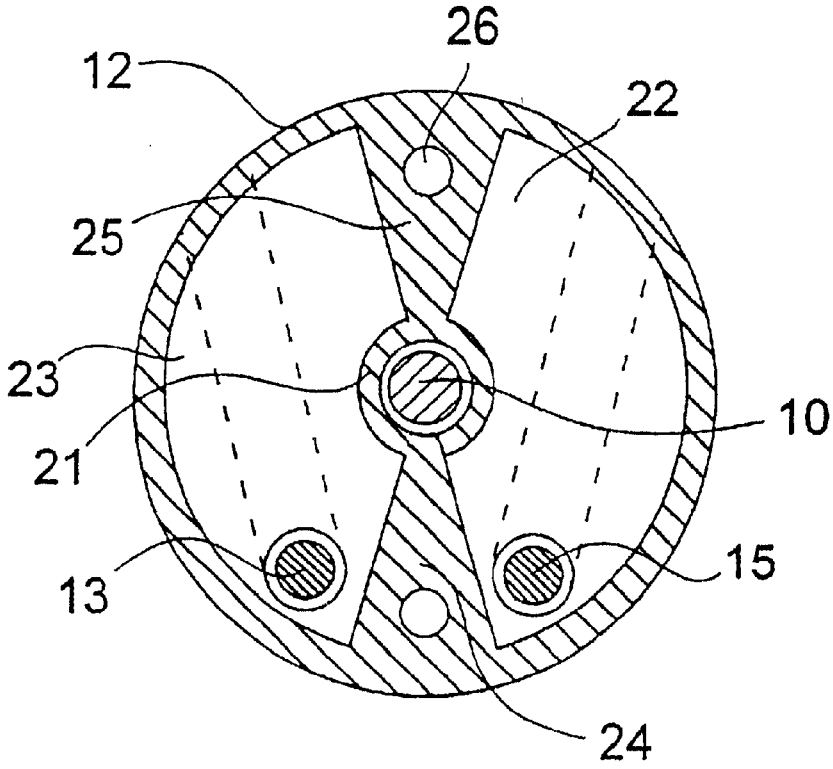
FIG. 2 is a cross-sectional view from line II—II of FIG. 1.

The cross-section view of FIG. 2 shows an example of how catheter 12 may be designed. The heating device 10 and its conductor for energy supply are contained in a centrally provided, first channel or tube 21. Tube 21 is surrounded by two radially displaced, communicating cavities 22, 23. Through these cavities there is distributed a cooling medium or coolant for cooling the tissue in direct contiguity to the heating device 10 in such applications for which heat treatment is directed towards the tissue at a certain radial distance from the heating device 10 and catheter 12. This is specifically applicable in cases when the heating device 10 includes an antenna.

The cooling medium is mainly used to avoid heating of tissue surrounding the catheter on its way to the treatment area, and which would be due to heat loss or similar from the conductor of the heating device 10.

Different portions of the catheter periphery are joined by two portions 24, 25, in which there are provided elongate channels 26 to allow for inflation and deflation of balloon 18. Portions 24, 25 merge into the central tube 21.

Figure 3:
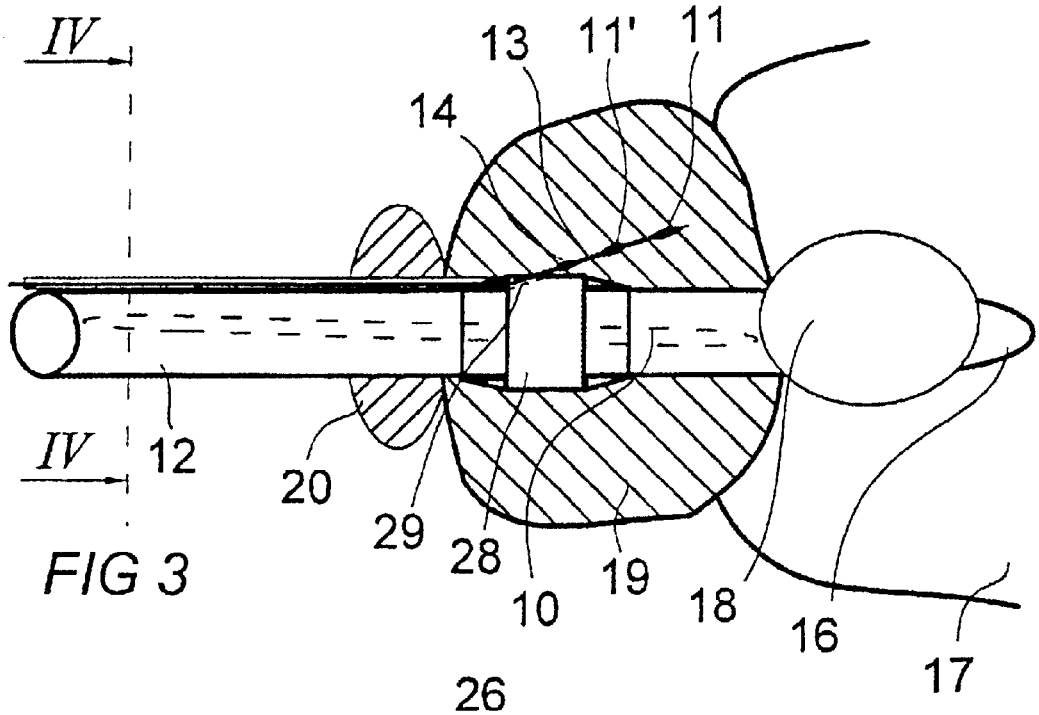
FIG. 3 is a principal longitudinal view of a practical embodiment of a device according to the invention.

In the practical embodiment of the device according to the invention, shown in FIG. 3, a tubing 27 made of Teflon or a similar material is provided external to the catheter. Tubing 27 is connected to a sleeve 28 mounted on catheter 12. Sleeve 28, in a portion outside of the orifice of tubing 27, is provided with an inclined portion 29. Preferably the sleeve is arranged with relation to the heating device 10 in such a way that the sleeve, in its operative mode, is located in the periphery or outside of the working area of heating device 10.

The annular *sleeve* member [20] *28* also has a stiffening effect, which prevents undesirable downward bending of catheter 12 in conjunction with forward push advancement of carrier 13. The length of annular member [20] *28* is adjusted to retain the suppleness and pliability of catheter 12.

Carrier 13, which is equipped with one or several temperature sensing means 11; 14, extends through tubing 27. Carrier 13 is rigid and has a pointed end. When the carrier is pushed in and passed through tubing 27 and reaching the inclined portion 29, which is preferably composed of a relatively hard material, carrier 13 is bent into a certain angle projecting out from the longitudinal direction of catheter 12. An advantageous angle has to be at least approximately 20°. A preferred angle is 30°. During continued insertion of carrier 13, its pointed end tip will penetrate the tissue outside of sleeve 28, and will penetrate further into the tissue as forward advancement continues. Selection of materials for carrier 13 and tubing 27 is done so that friction between them becomes suitably low.

As shown by FIG. 3, carrier 13 is equipped with several temperature transducers. These are arranged with a distance between them. A first temperature transducer 11 is provided at the pointed end tip of carrier 13, and a second temperature transducer 14 is provided at a distance from the pointed end tip corresponding to a normal distance of advancement by push of the carrier out of sleeve 28. Thereby this second temperature transducer 14 will be located in the periphery or outside of the area of treatment. There is provided an additional temperature transducer 11' between the two abovementioned temperature transducers 11;14. In the normal operative mode this third temperature transducer 11' is located in the middle of the area of treatment.

Figure 4:
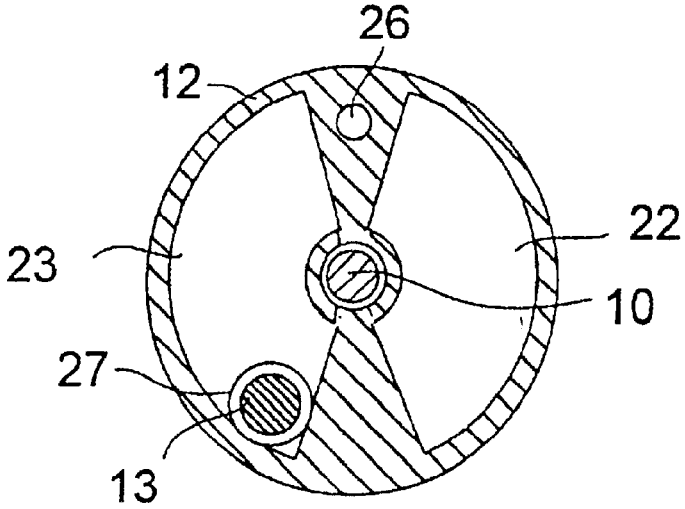
FIG. 4 is a cross-sectional view, from line IV—IV of FIG. 3, of an alternate embodiment of a device according to the invention.
Figure 5:
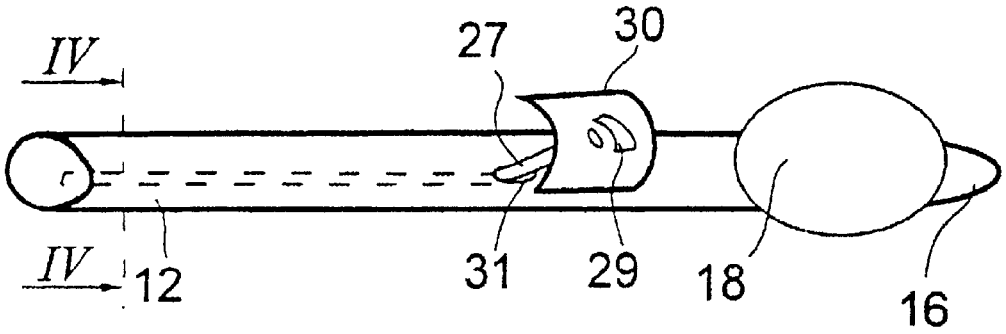
FIG. 5 is a principal longitudinal view of an alternate, practical embodiment of a device according to the invention, during assembly.

In the embodiment as per FIGS. 4 and 5, tubing 27 is arranged to run internally in catheter 12, most preferably within one of the channels 22 or 23. Tubing 27 at one end is attached to an end piece, which like sleeve 28 comprises a sloping or inclined portion 29. End piece 30 constitutes part of catheter 12, or is joined to catheter 12 so that the inclined portion 29 is located outside of an opening 31 made in catheter 12. Tubing 27 runs through this opening 31. During manufacture of a catheter according to this embodiment it is suitable that tubing 27 is led into the opening 31 from the outside and then led back through the catheter and out through an open end of the catheter. There is indication about such a procedure in FIG. 5, wherein end piece 30 has not yet been fastened to the exterior of catheter 12. Some materials used for tubing 27 must have a mechanical connection, for instance clamping, of the tubing against or onto end piece 30. Upon connection, tubing 27 should exhibit such a direction that a carrier, which is pushed out through the orifice of tubing 27, hits the inclined portion 29 and is outwardly directed at a desirable angle.

The end piece 30 and the orifice of tubing 27 are preferably covered by a diaphragm or a membrane. This allows for simple sterilization and cleaning of catheter 12 prior to usage. Upon insertion of catheter 12 into the treatment position, the diaphragm will be penetrated by carrier 13 in conjunction with the forward advancement of the carrier and temperature sensing means. In one embodiment, end piece 30 is provided as a supple plate, which covers part of the circumference of catheter 12.

For some applications it may prove insufficient with two temperature sensing means. Several elongate cavities for carriers and related sensing means will then be provided in the catheter. The heating device could also be provided in several separated elements. These could be arranged in multiple tubes or channels as well.

Figure 6:
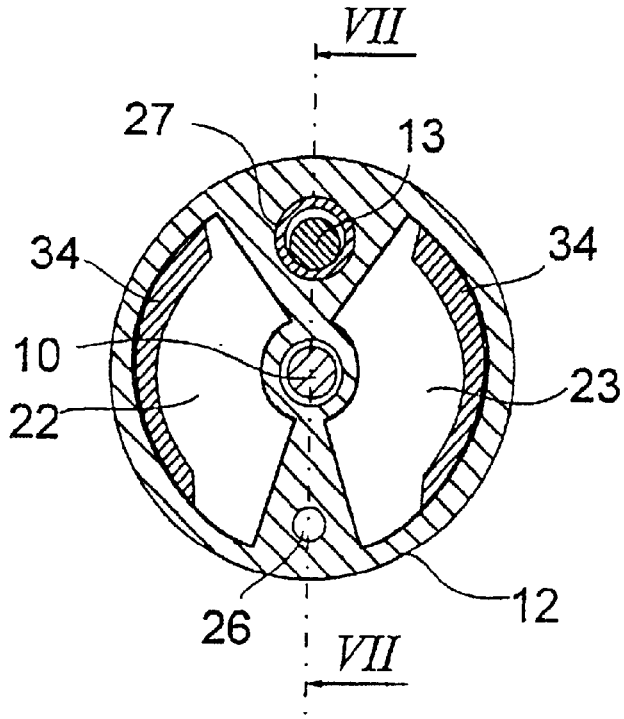
FIG. 6 is a cross-sectional view, from line VI—VI in FIG. 7, of yet another alternate embodiment of a device according to the invention.

In the embodiment as per FIG. 6, tubing 27 is provided in a special cavity of catheter 12. Tubing 27 runs through virtually the entire catheter 12. A peg 32 (see FIG. 7) is inserted into tubing 27 from the end facing the tip 16. Peg 32 is an end member in the tubing and is provided with an oblique, pointed end face 33, which has the same function as the inclined portion 29 in the embodiments described above. If stiffening of catheter 12 is required in this embodiment, one or several stiffening members 34 are preferably provided in catheter 12, so that catheter 12 obtains completely smooth exterior. Advantageously, the stiffening members 34 are arranged in channels 22 and 23, as shown in FIG. 6.

Figure 7:
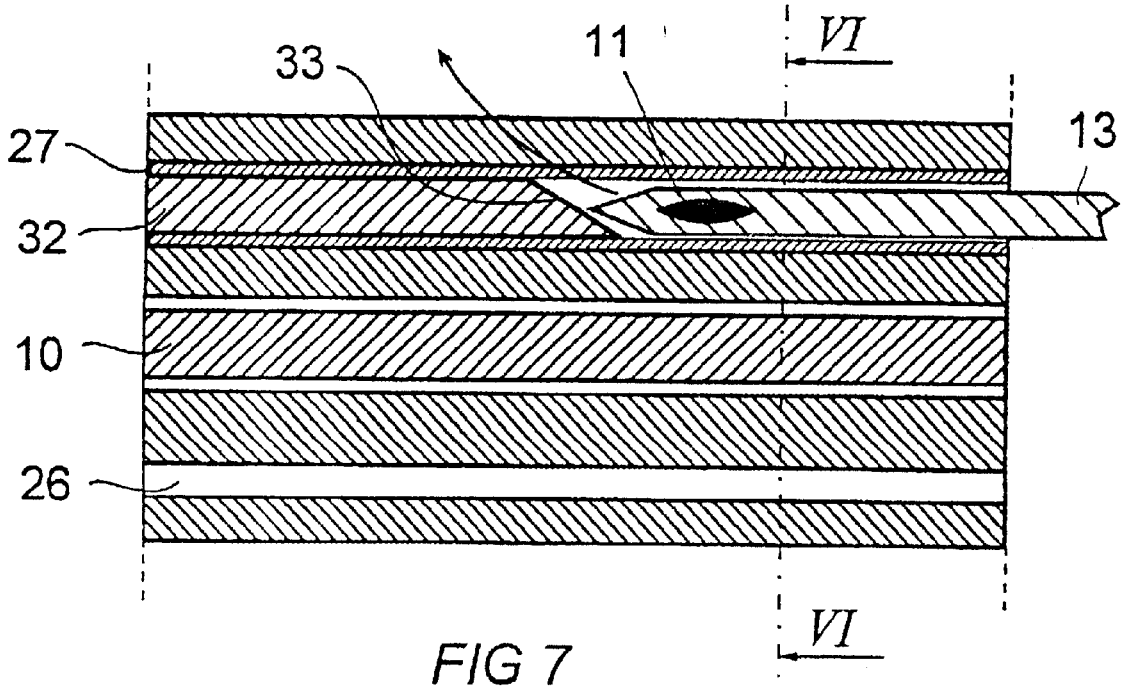
FIG. 7 is a longitudinal partial view, taken from line VII—VII, of the device of FIG. 8.

In FIG. 7, only part of catheter 12 is shown as designed in accordance with FIG. 6. Carrier 13 has been introduced into tubing 27 unto a position in which the pointed end tip engages the pointed end face of peg 32. As in the embodiments described above, carrier 13 upon further insertion of tubing 27 will be forced to deviate from an axial direction and adopt a deflected angle determined by the inclination of the sloping portion 29, which in this embodiment is represented by the pointed end face of peg 32. Carrier 13, in the shown embodiment, penetrates both the tubing 27 and the wall of catheter 12. In other embodiments, catheter 12 may be provided with a weakened portion in the area which is to be penetrated. It is also possible to make an opening, in advance, in catheter 12 and/or in tubing 27. The opening is preferably covered by a membrane or similar during insertion into the urethra or equivalent.

The increased resistance, which appears during deflection against the inclined portion 29 or pointed end face 33, can be used to define a starting point from which to determine the depth of insertion into the tissue, of carrier 13 with its pointed tip and temperature sensing means 11. This depth is also determined by the deflection angle. The signals generated at least by the first temperature sensing means 11 are conducted to an indicator unit, by means of which the attending staff can continuously assess the treatment. Preferably, the signals are also sent to a control unit not detailed herein, and which controls supply of power to the heating device 10. In the case of multiple temperature sensing means being used, it would be preferable to connect them to the indicator unit and/or control unit.

I claim:

[1. A device for heat treatment of prostate tissue comprising:

heating means for local heating of the prostate tissue;

a urological catheter enclosing said heating means; and a first temperature sensing means connected to a first carrier, said first carrier for sensing the temperature of the prostate tissue being movable through radially and out a wall of said catheter and said first carrier having a first end forming a first pointed tip, wherein said first pointed tip being adapted for insertion into the prostate tissue that is to be heat treated and that is located radially of said urological catheter.]

2. [The device according to claim 1 further comprising:] *A device for heat treatment of prostate tissue comprising:*

*heating means for local heating of the prostate tissue;*

*a urological catheter with a longitudinal axis and completely enclosing said heating means;*

*a first temperature sensing means connected to a first carrier, said first carrier for sensing the temperature of the prostate tissue, said first carrier being movable through and radially out a wall of said catheter relative to the longitudinal axis, and said first carrier having a first end forming a first pointed tip,*

*wherein said first pointed tip being adapted for insertion into the prostate tissue that is to be heat treated and that is located radially of said catheter upon movement of said first carrier through and out the wall of said catheter; and* a second temperature sensing means connected to a second carrier, said second carrier *for sensing the temperature of prostate tissue which is to be excluded from said heat treatment, said second carrier* being movable through and out of said [catheter] *catheter,* and said second carrier having a first end formed with a second pointed tip, wherein said second tip being adapted for insertion into prostate tissue which is to be excluded from said heat treatment *upon movement of said second carrier through and out of said catheter.*

[3. The device according to claim 1, wherein said first carrier is contained in cavities in said catheter.]

4. The device according to claim [1] *2* wherein said first carrier is contained in a tubing located on said catheter.

5. The device according to claim 4 wherein said tubing debouches into an end piece, said end piece having an inclined portion for angulation of said first carrier.

6. The device according to claim 5 wherein said end piece is provided externally on said catheter and said end piece is made of a material that is more rigid than said catheter so as to avoid undesired kinking of said catheter.

7. The device according to claim 5 wherein said end piece is provided internally in said catheter.

8. The device according to claim 7 further comprising:

at least one stiffening member positioned internally in said catheter.

9. The device according to claim [1] *2* wherein said heating means comprises at least one microwave antenna for delivery of energy to the body tissue.

10. The device according to claim 9 further comprising:

at least one heat-absorbing means in the vicinity of said microwave antenna for dissipation of heat from prostate tissue closest to said antenna.

11. The device according to claim 10 wherein said at least one heat-absorbing means comprises channels which extend through said catheter [and] *to contain* a cooling medium [being] distributed through said channels.

12. The device according to claim 11 wherein stiffening means is positioned in said channels in said catheter.

13. The device according to claim [1] *2* wherein at least one heat-absorbing means is provided for dissipation of heat from the prostate tissue closes to a supply lead connected to said heating means.

14. The device according to claim [1] *2* wherein said *first and second* temperature sensing means [is] *are* connected to a control unit, said control unit controlling the power of said heating means.

15. A method for heat treatment of prostate tissue *surrounding a urethra that extends from a distal bladder to a proximal exterior of a body*, comprising the steps of:

*extending a catheter into the urethra from the exterior of the body into the bladder;*

[local] *locally* heating [of] the prostate tissue with at least one heating means[, said heating means being ] *which is* enclosed in [a] *said* catheter;

continuously sensing of the *temperature of the locally-heated* prostate tissue [temperature] *at a plurality of different radially outward spaced locations relative to the urethra* with a temperature sensing means; and advancing said temperature sensing means which is connected with a [first] carrier through and radially out of said catheter and into the prostate tissue; [which is to be treated and is located radially external to said catheter for] *and*

[continuous control] continuously controlling *the temperature* of the *locally-heated prostate* tissue *based on the* temperature *sensed at the plurality of different locations.*

*16. The device according to claim 2, wherein said first and second carriers are contained in at least one cavity which extends longitudinally along said catheter.*

*17. The device according to claim 16 wherein said first carrier is contained in a tubing which is located in one said cavity, and said second carrier is contained in a tubing which is located in one said cavity.*

*18. The device according to claim 2 wherein said heating means comprises a comprises a receptacle within the catheter for containing heated liquid.*

*19. The device according to claim 2 wherein said heating means comprises an intermediary device which expands into abutment against the urethra.*

*20. A method as defined in claim 15 further comprising:*

*using separate temperature sensors positioned at spaced apart positions along a distal end portion of the carrier to sense each of the plurality of temperatures by a separate temperature sensor.*

*21. A method as defined in claim 20 further comprising:*

*sensing a first temperature of the locally-heated prostate tissue at a relatively greater radial outward location through which the distal end portion of the carrier has penetrated; and*

*sensing a second temperature of the locally-heated prostate tissue at a relatively lesser radial outward location through which the distal end portion of the carrier has penetrated.*

*22. A method as defined in claim 21 further comprising:*

*sensing a third temperature of the locally-heated prostate tissue at a relatively intermediate location through which the distal end portion of the carrier has penetrated, the intermediate location existing between the locations where the first and second temperatures are sensed.*

*23. A method as defined in claim 20 further comprising:*

*locally heating the prostate tissue in an area of heat treatment;*

*penetrating the distal end portion of the carrier into the prostate tissue at a periphery of the area of heat treatment as well as within the area of heat treatment;*

*sensing the plurality of temperatures of the locally-heated prostate tissue within the area of heat treatment; and additionally*

*sensing the temperature of the prostate tissue at the periphery of the area of heat treatment.*

*24. A method as defined in claim 23 further comprising:*

*sensing the temperature outside of the periphery of the area of heat treatment.*

*25. A method as defined in claim 23 further comprising:*

*penetrating the prostate tissue with the distal end portion of the carrier in a longitudinal direction as well as the radially outward direction relative to the urethra; and*

*sensing the plurality of temperatures at a plurality of different radially spaced and longitudinally separated locations within the area of heat treatment.*

*26. A method as defined in claim 25 further comprising:*

*penetrating the prostate tissue with the distal end portion of the carrier in the longitudinal direction toward the bladder.*

*27. A method as defined in claim 26 further comprising:*

*penetrating the prostate tissue with the distal end portion of the carrier at an angle of at least 20 degrees relative to the catheter.*

*28. A method as defined in claim 26 further comprising:*

*penetrating the prostate tissue with the distal end portion of the carrier at an angle of approximately 30 degrees relative to the catheter.*

*29. A method as defined in claim 15 further comprising:*

*emitting energy from an antenna within the catheter to locally heat the prostate tissue.*

*30. A method as defined in claim 15 further comprising:*

*conducting heat from a heated liquid within the catheter to locally heat the prostate tissue.*

*31. A method as defined in claim 15 further comprising:*

*locally heating the prostate tissue by delivering energy from a heating device positioned within the catheter.*

*32. A method as defined in claim 15 further comprising:*

*expanding an intermediary device into abutment against the urethra while locally heating the prostate tissue.*

*33. A method as defined in claim 15 further comprising:*

*pushing the carrier longitudinally at the exterior of the body to advance said temperature sensing means into the prostate tissue.*

*34. A method as defined in claim 15 further comprising:*

*retaining the catheter in the urethra relative to the bladder by expanding a balloon at the distal end of the catheter within the bladder and by penetrating the prostate tissue with a distal end portion of the carrier in a longitudinal direction toward the bladder.*

*35. A method as defined in claim 15 further comprising:*

*continuing the penetration of a distal end portion of the carrier into the prostate tissue in substantially the direction initiated upon advancing the carrier by utilizing substantially only an inherent stiffness characteristic of the distal end portion of the carrier.*

*36. A catheter for use during heat treatment of prostate tissue of a living body, the prostate tissue surrounding a urethra that extends from a distal bladder to a proximal exterior of the body, the catheter comprising:*

*a length sufficient to extend through the urethra from the exterior of the body and into the bladder;*

*an expandable balloon positioned at a distal end of the catheter to be expanded within the bladder to retain the catheter in the urethra relative to the bladder;*

*a channel extending from the exterior of the body along the catheter and terminating at a distal end located at a predetermined position spaced proximally from the expandable balloon;*

*a carrier extending from the exterior of the body through the channel and having a distal end portion to be advanced out of the terminating distal end of the channel and into the prostate tissue by applying advancement force to the carrier at the exterior of the body;*

*a deflecting element located at the terminating distal end of the channel to deflect the distal end portion of the carrier into the prostate tissue in a direction radially outward relative the catheter when the balloon retains the catheter relative to the bladder and upon advancement of the carrier out of the terminating distal end of the channel; and*

*a plurality of temperature sensors positioned in a spaced apart relationship along the distal end of the carrier to determine the temperature of the prostate tissue at a plurality of different radially outward spaced locations into which the distal end of the carrier has penetrated.*

*37. A catheter as defined in claim 36 wherein:*

*a first one of the temperature sensors is positioned distally at the distal end portion of the carrier; and*

*the carrier has stiffness characteristics which advance the distal end portion into the prostate tissue to locate the first temperature sensor at a maximum radial outward location upon advancement of the carrier.*

*38. A catheter as defined in claim 37 wherein:*

*a second one of the temperature sensors is positioned proximally from the distal end portion of the carrier to be located in the prostate tissue at a minimum radial outward location.*

*39. A catheter as defined in claim 38 wherein:*

*a third one of the temperature sensors is positioned between the first and second temperature sensors on the distal end portion of the carrier to be located in the prostate tissue at a lesser radial outward location than the first temperature sensor and a greater radial outward location than the second temperature sensor.*

*40. A catheter as defined in claim 36 further comprising:*

*a heating device in the catheter which is spaced relative to the expandable balloon at a predetermined position to deliver heat to the prostate tissue in an area of heat treatment surrounding the urethra when the catheter is retained relative to the bladder; and*

*at least two temperature sensors are located within the area of heat treatment.*

*41. A catheter as defined in claim 40 wherein:*

*the two temperature sensors are located within the area of heat treatment at different radially outward spaced locations relative to the urethra and at different locations longitudinally along the urethra.*

*42. A catheter as defined in claim 41 wherein:*

*at least one temperature sensor is located at a periphery of the area of heat treatment.*

*43. A catheter as defined in claim 42 wherein:*

*the temperature sensor located at the periphery of the area of heat treatment is outside of the area of heat treatment.*

*44. A catheter as defined in claim 41 wherein:*

*a first one of the temperature sensors is located at a relatively greater radial outward spaced location relative to the urethra;*

*a second one of the temperature sensors is located within the area of heat treatment at a relative middle radial outward spaced location relative to the urethra; and*

*a third temperature sensor is located at a periphery the area of heat treatment.*

*45. A catheter as defined in claim 44 wherein:*

*the third temperature sensor is located outside of the area of heat treatment.*

*46. A catheter as defined in claim 40 wherein:*

*the deflecting element deflects the distal end portion of the carrier to penetrate into the prostate tissue in a longitudinal direction as well as the radially outward direction.*

*47. A catheter as defined in claim 46 wherein:*

*the deflecting element comprises a curved distal portion of the channel.*

*48. A catheter as defined in claim 46 wherein:*

*the deflecting element comprises an inclined member positioned at the distal portion of the channel to deflect the distal end portion of the carrier into the longitudinal and radial outward direction into the prostate tissue upon advancement of the carrier.*

*49. A catheter as defined in claim 48 wherein:*

*the inclined member comprises an inclined surface positioned on the exterior of the catheter.*

*50. A catheter as defined in claim 48 wherein:*

*the inclined member comprises a peg having an inclined surface positioned within the channel.*

*51. A catheter as defined in claim 40 further comprising:*

*an opening in the catheter located at the terminating distal end of the channel and located at the predetermined position spaced proximally from the expandable balloon; and*

*a membrane which covers the opening and through which the distal end portion of the carrier penetrates upon advancement of the distal end portion of the carrier out of the channel and into the prostate tissue.*

*52. A catheter as defined in claim 51 wherein:*

*the heating device is positioned distally of the opening and within the prostate tissue when the catheter is retained relative to the bladder.*

*53. A catheter as defined in claim 40 wherein:*

*the deflecting element deflects the distal end portion of the carrier in the longitudinal direction toward the balloon.*

*54. A catheter as defined in claim 53 wherein:*

*the advancement of the distal end portion of the carrier in the radially outward and longitudinal direction defines an angle of at least 20 degrees with respect to a longitudinal axis of the catheter.*

*55. A catheter as defined in claim 53 wherein:*

*the advancement of the distal end portion of the carrier in the radially outward and longitudinal direction defines an angle of approximately* 30 degrees with respect to a longitudinal axis of the catheter.

*56. A catheter as defined in claim 40 wherein:*

*the heating device comprises an antenna from which energy is emitted into the prostate tissue.*

*57. A catheter as defined in claim 40 wherein:*

*the heating device comprises a receptacle within the catheter for containing heated liquid.*

*58. A catheter as defined in claim 40 wherein:*

*the heating device comprises an intermediary device which expands into abutment against the urethra.*

*59. A catheter as defined in claim 40 wherein:*

*the distal end portion of the carrier has sufficient stiffness to advance the distal end portion into the prostate tissue in approximately the direction of deflection initiated by the deflecting element.*

*60. A catheter as defined in claim 40 further comprising:*

*an opening in the catheter located at the terminating distal end of the channel and located at the predetermined position spaced proximally from the expandable balloon; and*

*a stiffener element connected to the catheter adjacent to the opening, the stiffener element reinforcing the catheter against bending at a position adjacent the opening upon advancement of the distal end portion of the carrier out of the opening.*

*61. A catheter as defined in claim 20 wherein:*

*the stiffener element is positioned exteriorly on the catheter.*

*62. A catheter as defined in claim 20 wherein:*

*the stiffener element is positioned interiorly within the catheter.*

*63. A catheter as defined in claim 36 wherein:*

*the distal end portion of the carrier has sufficient stiffness to continue to penetrate into the prostate tissue in substantially the direction initiated by the deflecting element upon advancement of the carrier.*

*64. A catheter as defined in claim 36 wherein:*

*the advancement force is a longitudinal push force applied to the carrier exteriorly of the body.*

*65. A method of monitoring heat treatment of prostate tissue of a living body, the prostate tissue surrounding a urethra that extends from a distal bladder to a proximal exterior of the body, the method comprising:*

*extending a catheter into the urethra from the exterior of the body into the bladder;*

*advancing a carrier proximally through the catheter from the exterior of the body by applying advancement force to the carrier at the exterior of the body;*

*penetrating the distal end portion of the carrier out of the catheter and into the prostate tissue to a desired depth in a direction radially outward relative the catheter by advancing the carrier; and*

*separately sensing temperatures of the prostate tissue at a plurality of different radially outward spaced locations relative to the urethra after the distal end portion of the carrier has penetrated into the prostate tissue to the desired depth.*

*66. A method as defined in claim 65 further comprising:*

*using separate temperature sensors positioned at spaced apart positions along the distal end portion of the carrier to sense each of the plurality of temperatures by a separate temperature sensor.*

*67. A method as defined in claim 65 further comprising:*

*sensing a first temperature of the prostate tissue at a relatively greater radial outward location after the distal end portion of the carrier has penetrated into the prostate tissue to the desired depth; and*

*sensing a second temperature of the prostate tissue at a relatively lesser radial outward location after the distal end portion of the carrier has penetrated into the prostate tissue to the desired depth.*

*68. A method as defined in claim 67 further comprising:*

*sensing a third temperature of the prostate tissue at a relatively intermediate location after the distal end portion of the carrier has penetrated into the prostate tissue to the desired depth, the intermediate location existing between the locations where the first and second temperatures are sensed.*

*69. A method as defined in claim 65 further comprising:*

*heating the prostate tissue in an area of heat treatment surrounding the urethra; and*

*sensing the plurality of temperatures of the prostate tissue within the area of heat treatment.*

*70. A method as defined in claim 69 further comprising:*

*penetrating the distal end portion of the carrier into the prostate tissue at a periphery of the area of heat treatment as well as within the area of heat treatment;*

*sensing the plurality of temperatures of the prostate tissue within the area of heat treatment; and additionally*

*sensing the temperature of the prostate tissue at the periphery of the area of heat treatment.*

*71. A method as defined in claim 70 further comprising:*

*sensing the temperature outside of the periphery of the area of heat treatment.*

*72. A method as defined in claim 69 further comprising:*

*penetrating the prostate tissue with the distal end portion of the carrier in a longitudinal direction as well as the radially outward direction relative to the urethra; and*

*sensing the plurality of temperatures at a plurality of different radially spaced and longitudinally separated locations within the area of heat treatment.*

*73. A method as defined in claim 72 further comprising:*

*penetrating the prostate tissue with the distal end portion of the carrier in the longitudinal direction toward the bladder.*

*74. A method as defined in claim 73 further comprising:*

*penetrating the prostate tissue with the distal end portion of the carrier at an angle of at least 20 degrees relative to the catheter.*

*75. A method as defined in claim 73 further comprising:*

*penetrating the prostate tissue with the distal end portion of the carrier at an angle of approximately 30 degrees relative to the catheter.*

*76. A method as defined in claim 69 further comprising:*

*emitting energy from an antenna within the catheter to heat the prostate tissue within the area of heat treatment.*

*77. A method as defined in claim 69 further comprising:*

*conducting heat from a heated liquid within the catheter to heat the prostate tissue in the area of heat treatment.*

*78. A method as defined in claim 69 further comprising:*

*heating the prostate tissue within the area of heat treatment by delivering energy from a heating device positioned within the catheter.*

*79. A method as defined in claim 69 further comprising:*

*expanding an intermediary device into abutment against the urethra while heating the prostate tissue in the area of heat treatment.*

*80. A method as defined in claim 65 further comprising:*

*pushing the carrier longitudinally at the exterior of the body to accomplish advancing the carrier and penetrating the distal end portion of the carrier into the prostate tissue.*

*81. A method as defined in claim 65 further comprising:*

*retaining the catheter in the urethra relative to the bladder by expanding a balloon at the distal end of the catheter within the bladder and by penetrating the prostate tissue with the distal end portion of the carrier in the longitudinal direction toward the bladder.*

*82. A method as defined in claim 65 further comprising:*

*continuing the penetration of the distal end portion of the carrier into the prostate tissue in substantially the direction initiated upon advancing the carrier by utilizing substantially only an inherent stiffness characteristic of the distal end portion of the carrier.*

* * * * *